United States Patent
Pizzoni

(10) Patent No.: US 10,471,092 B2
(45) Date of Patent: Nov. 12, 2019

(54) COMBINATION OF HYALURONIC ACID AND MACROGOL AND PHARMACEUTICAL COMPOSITIONS CONTAINING IT

(71) Applicant: APHARM S.r.l., Arona (IT)

(72) Inventor: Angelo Pizzoni, Arona (IT)

(73) Assignee: APHARM S.r.l., Arona (IT)

( * ) Notice: Subject to any disclaimer, the term of this patent is extended or adjusted under 35 U.S.C. 154(b) by 44 days.

(21) Appl. No.: 15/544,344

(22) PCT Filed: Nov. 3, 2015

(86) PCT No.: PCT/IB2015/058488
§ 371 (c)(1),
(2) Date: Jul. 18, 2017

(87) PCT Pub. No.: WO2016/120684
PCT Pub. Date: Aug. 4, 2016

(65) Prior Publication Data
US 2018/0008626 A1    Jan. 11, 2018

(30) Foreign Application Priority Data

Jan. 27, 2015    (IT) .............................. MI2015A0096

(51) Int. Cl.
| | | |
|---|---|---|
| A01N 43/04 | (2006.01) | |
| A61K 31/715 | (2006.01) | |
| A61K 31/728 | (2006.01) | |
| A61K 31/77 | (2006.01) | |
| A61K 31/75 | (2006.01) | |
| A61K 31/765 | (2006.01) | |

(52) U.S. Cl.
CPC ............ *A61K 31/728* (2013.01); *A61K 31/75* (2013.01); *A61K 31/765* (2013.01); *A61K 31/77* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 6,444,198 B1 * | 9/2002 | Daggy | ................. | A61K 9/0004 424/78.01 |
| 2002/0085990 A1 | 7/2002 | Daggy et al. | | |
| 2014/0057859 A1 | 2/2014 | Lewis | | |

FOREIGN PATENT DOCUMENTS

| | | | | |
|---|---|---|---|---|
| EP | 2545925 A1 * | 1/2013 | .......... | A61K 31/728 |
| EP | 2545925 A1 | 1/2013 | | |
| JP | 2002223727 A | 8/2002 | | |
| WO | 87/00754 A1 | 2/1987 | | |
| WO | 2013/037479 A1 | 3/2013 | | |
| WO | WO-2013037479 A1 * | 3/2013 | .......... | A61K 9/0048 |

OTHER PUBLICATIONS

Yeamin Huh, et al., Preparation and Evaluation of Spray-Dried . . . , European Journal of Pharmaceutical Sciences, vol. 40, No. 1, 2010.
Database WPI Week 200821, Thomson Scientific, AN 2008-C80517, XP002740307, 2007.
Database WPI Week 201424, Thomson Scientific, AN 2014-B44066, XP002740247, 2013.
International Search Report and Written Opinion for International Application No. PCT/IB2015/058488 (dated Feb. 17, 2016) (14 Pages).
Italian Search Report for Corresponding Italian Application No. IT MI20150096 (dated May 29, 2015) (3 Pages).

* cited by examiner

*Primary Examiner* — Patrick T Lewis
(74) *Attorney, Agent, or Firm* — Silvia Salvadori

(57) ABSTRACT

The invention relates to a new combination of hyaluronic acid and macrogol, pharmaceutical compositions containing said combination and the use of the combination and compositions as laxatives.

14 Claims, No Drawings

COMBINATION OF HYALURONIC ACID AND MACROGOL AND PHARMACEUTICAL COMPOSITIONS CONTAINING IT

CROSS-REFERENCE TO RELATED APPLICATIONS

This application is a 371 of PCT/IB2015/058488 filed Nov. 3, 2015, which claims the benefit of Italian Patent Application No. MI2015A000096 filed Jan. 27, 2015.

FIELD OF INVENTION

The present invention relates to a new combination of hyaluronic acid and macrogol, pharmaceutical compositions containing said combination and the use of the combination and compositions as laxatives.

BACKGROUND OF THE INVENTION

Hyaluronic acid is a non-sulfated glycosaminoglycan formed by a disaccharide straight sequence of 1-3-glucuronic acid bonded to N-acetylglucosamine. Hyaluronic acid is ubiquitous in epithelial and connective tissues, e.g., but not only, in skin and cartilages.

Macrogol is the International Non-proprietary Name (INN) of polyethylene glycol, conventionally abbreviated as PEG or PEO.

Macrogol having high molecular weight, in particular macrogol 3350, is used in therapy as a laxative to treat constipation, in particular chronic constipation and is commercialized for example under the Movicol® trademark. In order to obtain the laxative effect, macrogol is administered in a daily dose of 13.7 g-27.4 g daily (one or two sachets of Movicol® containing 13.7 g of macrogol daily). On the other hand, for the pediatric administration, macrogol is provided in 6.9 g sachets to be administered one or two times a day, depending upon the subject age and weight. Macrogol 4000 is also commercialized with the trademark Isocolan® as 34.8, 17.4 and 8.7 g sachets; the 34.8 g dose is considered suitable for the treatment of chronic constipation in adults, whereas the 17.4 and 8.7 g sachets are suitable for pediatric administration.

All the sachets are administered in admixture with water.

In order to carry out the preoperative bowel preparation or for diagnostic tests (colon cleansing), it is used as macrogol 4000 (Isocolan®) in a dose of about 280 g (8 sachets of 34.8 g), dissolved in abundant water.

Although it is a very effective drug for the treatment of constipation, at the therapeutic doses required in order to obtain the desired therapeutic effect, macrogol causes a hydrosaline imbalance, since it acts as osmotic agent keeping water in the colon; the amount of water and electrolytes embedded by macrogol, which directly depends upon the taken dose, can possibly cause a resulting arrhythmia and a reduced blood volume.

In order to try to overcome side effects, pharmaceutical compositions containing macrogol are added with electrolytes, such as sodium sulfate anhydrous, sodium bicarbonate, sodium chloride, potassium chloride and/or ascorbic acid. However, the possible hydrosaline imbalance caused by the intake of high doses of macrogol results in the fact that it must be used with great care in children, and in debilitated subjects, in elderly people, in kidney patient and heart patients. In addition to a possible hydrosaline imbalance, at the used doses, macrogol can produce abdominal bloating and pain and nausea.

There is therefore the need to optimize the therapeutic use of macrogol, e.g. by reducing doses to be administered while maintaining a valuable effectiveness against constipation.

OBJECTS OF THE INVENTION

It is an object of the invention to provide a laxative combination comprising macrogol, which does not produce the side effects of compositions currently present on the market.

It is another object of the invention to provide a laxative combination comprising macrogol at low dose and hyaluronic acid, which has the same effectiveness, if not higher, with respect to compositions currently present on the market.

It is a further object of the invention to provide pharmaceutical compositions comprising the combination of the invention and their use as laxatives.

DESCRIPTION OF THE INVENTION

Therefore, according to one of the aspects of the invention, its object is a combination of macrogol and hyaluronic acid, or a salt thereof, in particular a combination of high molecular weight macrogol and hyaluronic acid.

According to a preferred aspect, macrogol has a molecular weight comprised between 3,000 and 5,000 Da, preferably between 3,200 and 4,500 Da, more preferably 3,350 or 4,000 Da.

According to a preferred aspect, hyaluronic acid has a molecular weight comprised between 50,000 and 2,000,000 Da, preferably between 50,000 and 1,000,000 Da, more preferably between 50,000 and 300,000 Da, still more preferably between 80,000 and 120,000 Da, e.g. about 100,000 Da.

According to a most preferred aspect, hyaluronic acid is in the form of its sodium salt and has a molecular weight comprised between 50,000 and 300,000 Da, preferably between 80,000 and 120,000 Da, more preferably has an average molecular weight of about 100,000 Da.

If desired, it is clearly possible to mix macrogol and/or hyaluronic acid having different molecular weights.

A preferred combination according to the invention is a fixed combination wherein macrogol and sodium hyaluronate are in weight ratios respectively from 40/1 to 10/1 (w/w), preferably from 30/1 to 20/1 (w/w), more preferably in macrogol/sodium hyaluronate weight ratios around 25-26/1.

However, different ratios can be used.

Experiments carried out by the Applicant have in fact demonstrated that the combination of the invention can significantly increase the intestinal peristaltic and propulsive action and that the combination of the two components lead to a synergistic effect with respect to the activity of the two components considered separately, with statistical significance.

Moreover the combination facilitates the expulsion action at macrogol doses significantly lower than those required to achieve the same effect with the macrogol alone, which is particularly relevant. Indeed it has been observed that the addition of hyaluronic acid, or a salt thereof, allows to reduce the macrogol dose up to a third of the dose currently used in therapy.

The synergy provided by the combination is completely unexpected and represents a significant improvement in this technical field. In fact, the dose reduction of macrogol causes a significant reduction of side effects brought about by macrogol. Thanks to the synergy created by the combination of the two components, it has been possible to impressively reduce, by about 40%, the daily amount of macrogol to be administered. For this reason, the combination of the invention is already active at daily doses of about 8 g of macrogol, with effects comparable to those of 13.7 g Movicol®.

The use of the compositions of the invention as laxative against constipation, advantageously chronic constipation, represents a further subject-matter of the invention.

According to another of the aspects thereof, the invention relates to the combination of the invention for use in the treatment of adult constipation and adult chronic constipation, said use being characterized in that said combination contains 8 to 16 g of macrogol, preferably macrogol 3350, and 0.3 to 0.5 g of hyaluronic acid or a salt thereof, preferably sodium hyaluronate.

According to another of the aspects thereof, the invention relates to the combination of the invention for use in the treatment of children constipation and children chronic constipation, characterized in that the combination contains 4 to 8 g of macrogol, preferably macrogol 3350, and 0.150 to 0.300 g of hyaluronic acid or a salt thereof, preferably sodium hyaluronate.

For colon cleansing, the combination comprises macrogol 3350 or macrogol 4000 and the dose can be increased up to 200 g but preferably 140 g of macrogol and 2-5 g, preferably about 3 g, of sodium hyaluronate, to be administered in the afternoon or in the evening before the operation or the diagnostic test.

It is understood from the above and from the results of the assays carried out reported in the experimental section below, that the combination of the invention allows to significantly reduce the macrogol doses to be administered, with a resulting reduction of side effects.

Moreover, the administration of hyaluronic acid produce a lenitive effect on the intestinal mucosa, alleviating the irritations usually caused by conventional laxatives and the irritations caused by too hard and dry stool, which are typical of the disease. The combination of the invention can be administered in combination with other active ingredients or excipients, e.g. electrolytes, adsorbent agents for intestinal gases, such as simethicone, activated carbon and the like, or fibers such as partially hydrolyzed guar gum or other fibers as well.

The invention combination, for use thereof, is clearly mixed with water and the water/sodium hyaluronate/macrogol mixtures represent a further aspect of the invention, in particular in the preferred embodiments described above.

For use according to the invention, the combination is preferably administered in oral pharmaceutical compositions, e.g. in the form of granulates, tablets, capsules and the like, in combination with one or more pharmaceutically acceptable additives or carriers.

The use of the compositions of the invention as a laxative against constipation, advantageously chronic constipation, represents a further object of the invention.

It is a further aspect of the invention the use of the combination and compositions for colon cleansing, e.g. before endoscopic tests or surgery.

The compositions comprising the combination represent a further object of the invention. The compositions of the invention can be administered orally.

According to a preferred embodiment, said compositions comprise macrogol and sodium hyaluronate.

According to a most preferred embodiment, said compositions comprise 12-2 g of macrogol, advantageously macrogol 3350 and 0.5-0.1 g of hyaluronic acid or a salt thereof, advantageously sodium hyaluronate; preferably the compositions will comprise 8-4 g of macrogol, advantageously macrogol 3350 and 0.5-0.150 g of hyaluronic acid or a salt thereof, advantageously sodium hyaluronate. Such compositions can be administered once or more times a day, preferably 1-2 times a day, still more preferably 2 times a day, with water. However, a different dosage regime can be anyway chosen by the family doctor, according to the response of the subject. The intake of abundant water is important in order to aid the effect of the combination.

According to another embodiment, when colon cleansing is desired, the compositions of the invention comprise 300-100 g of macrogol, advantageously macrogol 3350 or 4000, and 2-5 g of hyaluronic acid or a salt thereof, advantageously sodium hyaluronate. Such compositions should be taken at regular intervals in the afternoon or the evening before the operation or the diagnostic test, together with abundant water.

According to another of the aspects thereof, the invention relates to the compositions of the invention for use in the treatment of adult constipation and adult chronic constipation, said use being characterized in that said compositions comprise 8 to 16 g of macrogol, preferably macrogol 3350, and 0.3 to 0.5 g of hyaluronic acid or a salt thereof, preferably of sodium hyaluronate.

According to another of the aspects thereof, the invention relates to the compositions of the invention for use in the treatment of children constipation and children chronic constipation, said use being characterized in that said compositions comprise 4 to 8 g of macrogol, preferably macrogol 3350, and 0.150 to 0.300 g of hyaluronic acid or a salt thereof, preferably of sodium hyaluronate.

For colon cleansing, the compositions of the invention preferably comprise macrogol 3350 or 4000 and the dose can be increased up to 300 g, preferably about 150 g of macrogol and up to 8 g, preferably about 6 g of sodium hyaluronate divided in multiple administrations to be administered in the afternoon or in the evening, before the operation or the diagnostic test. For example, two sachets containing a composition comprising 70 g of macrogol, advantageously macrogol 3350, and about 3 g of sodium hyaluronate, together with electrolytes and optionally conventional excipients, can be prepared. In this case, the dosage considers the intake of two sachets as described above, each one diluted with about a liter of water.

Particularly preferred compositions are in the form of granulates and comprise the above indicated amounts of macrogol and sodium hyaluronate.

Such granulates can be packaged in single- or multi-dose containers, advantageously in single-dose sachets and be administered as mixed with water.

The compositions of the invention can comprise other active ingredients or excipients as well, such as e.g. electrolytes, adsorbent agents for intestinal gases, such as simethicone, activated carbon and the like, as well as the excipients and the carriers conventionally used in the pharmaceutical technique.

The compositions can contain sodium, potassium, chloride, carbonate and ascorbate ions. Preferably, the compositions of the invention can contain sodium sulfate, sodium chloride and potassium chloride. For example, in an embodiment, but without limitation, the compositions can also contain ascorbate ions, e.g. ascorbic acid and sodium ascorbate, for the colon cleansing. Such ions can be contained in the same packaging or in a separate packaging. For example macrogol and sodium, potassium, chloride and carbonate ions can be contained in a sachet whereas the ascorbate ions can be contained in a separate sachet, the two sachets having to be dissolved in water or another liquid for the oral administration. Examples of compositions are provided in the experimental section.

According to an embodiment, the compositions of the invention can also contain fibers, such as partially hydrolyzed guar gum (PHGG) or other natural fibers or fibers that underwent industrial processing.

As mentioned, the compositions can also contain flavoring, sweetening agents, antioxidant agents etc.

Examples of compositions representative of the invention are provided in the Experimental section below.

The invention also comprises a method for the treatment of constipation, of chronic constipation and for colon cleansing, comprising administering an effective amount of the combination or the composition according to the invention to a subject in need thereof.

It is understood from the above and from the following experimental results that the combination of the invention represents a remarkable technical progress, since it allows to use macrogol at significantly reduced doses with respect to those commonly used, thus reducing the its relevant side effects, while keeping an excellent laxative effectiveness and producing in addition a lenitive effect on the intestinal mucosa.

Experimental Section

Example 1

Pharmaceutical Composition Comprising the Combination for Laxative Use

Each granulate sachet, to be dissolved in water and preferably administered twice a day, contains:
 8 g of macrogol 3350
 0.30 g of sodium hyaluronate (average MW 100,000 Da)
 0.2 g of sodium chloride
 0.10 g of sodium bicarbonate
 0.3 g of potassium chloride
 Excipients: acesulfame potassium, orange flavor.

Example 2

Pharmaceutical Composition Comprising the Combination for Laxative Use

Each granulate sachet, to be dissolved in water and preferably administered twice a day, contains:
 8 g of macrogol 3350
 0.2 g of sodium hyaluronate (average MW 100,000 Da)
 0.15 g of sodium chloride
 0.20 g of sodium bicarbonate
 0.20 g of potassium chloride
 Excipients: acesulfame potassium and lemon flavor.

Example 3

Pharmaceutical Composition Comprising the Combination for Colon Cleansing

Each granulate sachet to be dissolved in abundant water and to be administered in several doses, contains:
 150 g of macrogol 4000
 3 g of sodium hyaluronate (average MW 100,000 Da)
 5 g of sodium chloride
 2 g of potassium chloride
 15 g of potassium sulfate
 Excipients: acesulfame potassium, saccharin, orange flavor.

Example 4

Pharmaceutical Composition Comprising the Combination for Colon Cleansing

Each granulate sachet to be dissolved in abundant water and to be administered in several doses, contains:
 160 g of macrogol 4000
 3 g of sodium hyaluronate (average MW 100,000 Da)
 4 g of sodium chloride
 3 g of sodium bicarbonate
 3 g of potassium chloride
 10 g of potassium sulfate
 0.10 g of simethicone
 Excipients: acesulfame potassium, orange flavor.

Example 5

Pharmaceutical Composition Comprising the Combination for Colon Cleansing

Each granulate sachet to be dissolved in abundant water and to be administered in several doses, contains:
 70 g of macrogol 3350
 3 g of sodium hyaluronate (average MW 100,000 Da)
 3 g of sodium chloride
 2 g of sodium bicarbonate
 2 g of potassium chloride
 6 g of potassium sulfate
 0.10 g of simethicone
 For colon cleansing 2 sachets dissolved in water are administered.
 Excipients: acesulfame potassium, lemon flavor.

Example 6

Pharmaceutical Composition Comprising the Combination for Colon Cleansing

Each composition sachet, to be dissolved in abundant water and to be administered in several doses, contains:
 70 g of macrogol 3350
 3 g of sodium hyaluronate (average MW 100,000 Da)
 4 g of sodium chloride
 3 g of potassium chloride
 3 g of potassium sulfate
 The content of the above described sachet has to be administered in combination with the content of a second sachet containing 4.7 g of ascorbic acid and 5.9 g of potassium ascorbate.
 For colon cleansing 2 doses dissolved in water are administered.

Example 7

Pharmaceutical Composition Comprising the Combination for Laxative Use for pediatric administration.

Each granulate sachet, to be dissolved in water and preferably administered twice a day, contains:
 4 g of macrogol 3350
 0.15 g of sodium hyaluronate (average MW 100,000 Da)
 0.10 g of sodium chloride
 0.10 g of sodium bicarbonate
 0.10 g of potassium chloride

Example 8

Experimental Assays

Intestinal transit, colon peristalsis and the amount of stool expelled have been evaluated on rats, after the administration of different individual doses of macrogol and sodium hyaluronate and of the combination of the invention.

Intestinal Transits:

From Table 1 it is possible to observe that PEG administered by gavage in the rat, within the dose interval comprised between 365 and 1460 mg/kg p.o., does not induce a significant increase of intestinal motility. On the other hand, such a parameter is increased with a dose-response behavior at the same doses by adding 0.3 ml of water administered per os. as well. In fact, the percentage increase values range from +10% at the 365 mg/kg p.o. dose of PEG to +23% at the 1560 mg/kg p.o. dose. Also the treatment with sodium hyaluronate (20-50 mg/kg p.o.), without the simultaneous intake of water, does not induce an increase of the intestinal transit. Also in this case, as it has been observed above, the administration of 0.3 ml of water causes an increase of transit percentage ranging from +17.0% (20 mg/kg p.o. hyaluronate) to +20.3% (50 mg/kg p.o.). Interesting results, under the same experimental conditions, have been obtained with the combination of PEG and sodium hyaluronate. In particular the combination 730 mg/kg p.o. PEG+30 mg/kg p.o. hyaluronate induced a percentage increase of 33.4%, thus significantly higher than that obtained with PEG alone at the same dose (15.3%) still in presence of water. Such an effect is even higher if sodium hyaluronate is added in a higher dose with respect to the previous one and equal to 50 mg/kg p.o. If the combination PEG (973 mg/kg p.o.) and 50 mg/kg p.o. hyaluronate is taken into account, the increase of the intestinal transit reaches a value of +44.4%, much higher than the value obtained with PEG alone at the same dose. By reducing the PEG dose of one third with respect to 730 mg/kg and with the addition of sodium hyaluronate+water, a higher value has been observed with respect to that one obtained with PEG alone at 1560 mg/kg p.o., and such value is equal to 34.7% as the sodium hyaluronate dose (50 mg/kg p.o. instead of 30 mg/kg p.o.) is increased. The administration of a combination constituted by of PEG at the 365 mg/kg p.o. dose and hyaluronate at 50 mg/kg p.o. allows to obtain a value comparable to that observed with the combination 730 mg/kg p.o. PEG and 50 mg/kg p.o. sodium hyaluronate, thus demonstrating that is possible to obtain similar results by reducing on the one hand the PEG dose.

The experiment has been carried out following the method of Schulz et al (*NS Arch. Pharmacol.* 308:255-260, 1979) by using an activated carbon feed. 1.5 ml of a 20% (w/v) activated carbon suspension in a 5% (w/v) gum arabic solution has been administered by gavage to 24 hrs starved rats with free access to water. The rats have been sacrificed 10 min after receiving the activated carbon feed and their intestine has been completely removed. The transit in the small intestine has been calculated for each rat as the ratio between the traveled distance of the activated carbon feed and the total length of the intestine itself. Data are expressed as the percentage of transit in treated rats with respect to controls that have been considered as 100. Administration of the preparations occurred 30 min before sacrificing the animal.

TABLE 1

EFFECT OF PEG AND SODIUM HYALURONATE ON THE INTESTINAL TRANSITS

| TREATMENT | % of increase of intestinal transit with respect to |
|---|---|
| 365 mg/kg p.o. PEG | 9.4 |
| 730 mg/kg p.o. PEG | 6.7 |
| 973 mg/kg p.o. PEG | 8.8 |
| 1460 mg/kg p.o. PEG | 8.6 |
| 365 mg/kg p.o. PEG + Water | 10.8 |
| 487 mg/kg p.o. PEG + Water | 11.5 |
| 730 mg/kg p.o. PEG + Water | 15.3 |
| 973 mg/kg p.o. PEG + Water | 18.6 |
| 1560 mg/kg p.o. PEG + Water | 23.2 |
| 3120 mg/kg p.o. PEG + Water | Beginning of fecal incontinence |
| 20 mg/kg p.o. IALURONATE | 0 |
| 30 mg/kg p.o. IALURONATE | 3.8 |
| 50 mg/kg p.o. IALURONATE | 4.2 |
| 20 mg/kg p.o. IALURONATE + Water | 17.0 |
| 30 mg/kg p.o. IALURONATE + Water | 19.6 |
| 50 mg/kg p.o. IALURONATE + Water | 20.3 |
| 730 mg/kg p.o. PEG + 30 mg/kg p.o. IALURONATE + Water | 33.4 |
| 730 mg/kg p.o. PEG + 50 mg/kg p.o. IALURONATE + Water | 38.2 |
| 973 mg/kg p.o. PEG + 50 mg/kg p.o. IALURONATE + Water | 44.4 |
| 487 mg/kg p.o. PEG + 30 mg/kg p.o. IALURONATE + Water | 29.8 |
| 487 mg/kg p.o. PEG + 50 mg/kg p.o. IALURONATE + Water | 34.7 |
| 365 mg/kg p.o. PEG + 50 mg/kg p.o. IALURONATE + Water | 33.6 |

Tab. 1 Each datum is given as the average of 6-8 rats.
Water = 0.3 ml

Colon Propulsion

In Table 2 it is possible to note how PEG alone, i.e. without the simultaneous administration of water by gavage, does not modify the colon propulsion activity in rats whereas it can be observed a statistically significant effect when PEG, in the dose range comprised between 365 and 1560 mg/kg p.o., is injected in presence of a simultaneous intake of water. In this case all the values are significant with respect to the same treatment without water. The treatment by gavage of sodium hyaluronate at 20-50 mg/kg p.o. doses does not modify the expulsion time of the bead whereas, also in this case, the effect is very evident if the rat intakes water (0.2 ml). Analogously to what observed in tab. 1, it can be observed a synergistic effect induced by the combination PEG+sodium hyaluronate+water. The reduction of expulsion time results to be dose dependent, being in all the cases clearly evident and statistically significant with respect to the PEG+water dose. The reduction of one third of the PEG dose (487 mg/kg p.o.), if combined with 30 and 50 mg/kg p.o. hyaluronate, provides a value comparable to 973 and 1560 mg/kg p.o. PEG, respectively. If the PEG dose is further reduced to the half, the value obtained by the combination of 365 mg/kg p.o. PEG and 50 mg/kg p.o. hyaluronate is comparable to 973 mg/kg p.o. PEG+water. Propulsion of distal colon has been measured according to the method of Raffa et al. (*Life Sci.*, 41: 2229-34, 1987) and of Lopez (*Dig. Dis. Sci.*, 29:551, 1984). 30 min after the administration of the preparations, a 5 mm diameter glass bead has been inserted in the distal colon of each rat at 3 cm from the anus. The parameter taken as the reference was the time required by each rat to expel the bead. The lower the expulsion time, the highest the colon propulsion.

EFFECT OF PEG AND SODIUM HYALURONATE
ON THE COLON PROPULSION

| TREATMENT | Bead Expulsion time (s) |
|---|---|
| 365 mg/kg p.o. PEG | 202 ± 11 |
| 730 mg/kg p.o. PEG | 181 ± 9 |
| 973 mg/kg p.o. PEG | 185 ± 12 |
| 1460 mg/kg p.o. PEG | 173 ± 15 |
| 365 mg/kg p.o. PEG + Water | 153 ± 13*§ |
| 487 mg/kg p.o. PEG + Water | 135 ± 19* |
| 730 mg/kg p.o. PEG + Water | 128 ± 16*§ |
| 973 mg/kg p.o. PEG + Water | 116 ± 18*§ |
| 1560 mg/kg p.o. PEG + Water | 93 ± 9*§ |
| 3120 mg/kg p.o. PEG + Water | Immediate expulsion |
| 20 mg/kg p.o. IALURONATE | 195 ± 12 |
| 30 mg/kg p.o. IALURONATE | 191 ± 16 |
| 50 mg/kg p.o. IALURONATE | 188 ± 21 |
| 20 mg/kg p.o. IALURONATE + Water | 129 ± 14*§ |
| 30 mg/kg p.o. IALURONATE + Water | 120 ± 11*§ |
| 50 mg/kg p.o. IALURONATE + Water | 114 ± 15*§ |
| 730 mg/kg p.o. PEG + 30 mg/kg p.o. IALURONATE + Water | 94 ± 10*§ |
| 730 mg/kg p.o. PEG + 50 mg/kg p.o. IALURONATE + Water | 85 ± 12*§ |
| 973 mg/kg p.o. PEG + 50 mg/kg p.o. IALURONATE + Water | 66 ± 8*§ |
| 487 mg/kg p.o. PEG + 30 mg/kg p.o. IALURONATE + Water | 112.8 ± 13*§ |
| 487 mg/kg p.o. PEG + 50 mg/kg p.o. IALURONATE + Water | 97.7 ± 14*§ |
| 365 mg/kg p.o. PEG + 50 mg/kg p.o. IALURONATE + Water | 119.6 ± 16*§ |

Tab. 2 Each datum is given as the average of 6-8 rats.
Water = 0.3 ml
^ P < 0.05;
*P < 0.01-
§P < 0.05 vs PEG at the corresponding dose.

Evaluation of the Amount of Stool

In Table 3 it is possible to observe an increase in the number of expelled pellets from the rat after the PEG (365-1460 mg/kg p.o. without water and 365-1560 mg/kg p.o. with water) and 20-50 mg/kg hyaluronate treatment in both conditions. In all the preceding cases, a maximum of 3 expelled pellets in the 60 min observation has been revealed. A greater number of expelled pellets have been induced by the combination of 730 mg/kg p.o. PEG with 30 and 50 mg/kg p.o. sodium hyaluronate+water. Combination of a higher dose of PEG, equal to 973 mg/kg p.o.+50 mg/kg sodium hyaluronate+water, even caused the expulsion of liquid stool. By administering a dose of 487 mg/kg PEG+50 mg/kg p.o. sodium hyaluronate+water, the number of expelled pellets is equal to that one that can be observed with 730 mg/kg p.o. PEG and 30 mg/kg p.o. sodium hyaluronate. PEG at 365 mg/kg p.o. dose+50 mg/kg sodium hyaluronate results in a lower laxative action but still comparable to that one of PEG+water dose of 730-1560 mg/kg p.o. (effect ascribable to sodium hyaluronate only). The stool expulsion has been monitored for each rat, starting from 1 h after the administration of the preparations (*Martinez e Taché, Brain Res.* 893: 29-35, 2001).

EFFECT OF PEG AND SODIUM HYALURONATE
ON THE NUMBER OF EXPELLED PELLETS

| TREATMENT | No of pellets after 60 min |
|---|---|
| 365 mg/kg p.o. PEG | 0 |
| 730 mg/kg p.o. PEG | 0 |
| 973 mg/kg p.o. PEG | 1 |
| 1460 mg/kg p.o. PEG | 1 |
| 365 mg/kg p.o. PEG + Water | 0 |
| 487 mg/kg p.o. PEG + Water | 2 |
| 730 mg/kg p.o. PEG + Water | 3 |
| 973 mg/kg p.o. PEG + Water | 3 |
| 1560 mg/kg p.o. PEG + Water | 3 |
| 3120 mg/kg p.o. PEG + Water | Start of diarrhea |
| 20 mg/kg p.o. IALURONATE | 0 |
| 30 mg/kg p.o. IALURONATE | 1 |
| 50 mg/kg p.o. IALURONATE | 1 |
| 20 mg/kg p.o. IALURONATE + Water | 2 |
| 30 mg/kg p.o. IALURONATE + Water | 2 |
| 50 mg/kg p.o. IALURONATE + Water | 3 |
| 730 mg/kg p.o. PEG + 30 mg/kg p.o. IALURONATE + Water | 5 |
| 730 mg/kg p.o. PEG + 50 mg/kg p.o. IALURONATE + Water | 7 |
| 973 mg/kg p.o. PEG + 50 mg/kg p.o. IALURONATE + Water | Expulsion of liquid stool |
| 487 mg/kg p.o. PEG + 30 mg/kg p.o. IALURONATE + Water | 4 |
| 487 mg/kg p.o. PEG + 50 mg/kg p.o. IALURONATE + Water | 5 |
| 365 mg/kg p.o. PEG + 50 mg/kg p.o. IALURONATE + Water | 3 |

Tab. 3 Each given datum is the average of 4 rats.
Water = 2 ml

The invention claimed is:

1. A combination consisting of macrogol having molecular weight of between 3,000 and 5,000 Da and hyaluronic acid with an average molecular weight of between 50,000 and 300,000 Da or a salt thereof, wherein the macrogol and the sodium hyaluronate are in weight ratios from 40/1 to 10/1 (w/w/), respectively.

2. The combination according to claim 1 wherein the macrogol has a molecular weight selected between 3,350 and 4,000 Da.

3. The combination according to claim 1, wherein the hyaluronic acid is in the form of sodium salt thereof.

4. The combination according to claim 1, wherein hyaluronic acid, or the sodium salt thereof, has an average molecular weight of about 100,000 Da.

5. The combination according to claim 1, wherein the macrogol/sodium hyaluronate weigh ratios are from 30/1 to 20/1 (w/w).

6. An oral pharmaceutical composition comprising pharmaceutically acceptable excipients and/or carriers, macrogol having molecular weight of between 3,000 and 5,000 Da and hyaluronic acid with an average molecular weight of between 50,000 and 300,000 Da or a salt thereof, wherein the macrogol and the sodium hyaluronate are in weight ratios from 40/1 to 10/1 (w/w/), respectively.

7. The oral pharmaceutical composition according to claim 3, containing 12-2 g of macrogol and 0.5-0.1 g of hyaluronic acid or a salt thereof.

8. The oral pharmaceutical composition according to claim 7, containing 8-4 g of macrogol and 0.5-0.150 g of hyaluronic acid or a salt thereof.

9. The oral pharmaceutical composition according to claim 6, further comprising-electrolytes and/or absorbent agents of intestinal gases.

10. The oral pharmaceutical composition according to claim 6, wherein said macrogol is macrogol 3350 and said salt of hyaluronic acid is sodium hyaluronate.

11. A method for treatment of constipation or colon cleansing comprising administering to a person in need thereof
- a combination consisting of macrogol having molecular weight of between 3,000 and 5,000 Da, hyaluronic acid with an average molecular weight of between 50,000 and 300,000 Da, or a salt thereof, and water; or
- an oral pharmaceutical composition comprising pharmaceutically acceptable excipients and/or carriers, macrogol having molecular weight of between 3,000 and 5,000 Da, hyaluronic acid with an average molecular weight of between 50,000 and 300,000 Da or a salt thereof, and water.

12. The oral pharmaceutical composition according to claim 9, wherein said adsorbent agents of intestinal gases are simethicone, activated carbon and/or fibers.

13. The oral pharmaceutical composition according to claim 9, further comprising water.

14. A method of treating children constipation and children chronic constipation, said method comprising administering the composition of claim 6 to children in need thereof, wherein said composition contains from 4 to 8 g of macrogol and from 0.150 to 0.3 g of hyaluronic acid or a salt thereof.

* * * * *